United States Patent

Honma et al.

[11] Patent Number: 5,708,167
[45] Date of Patent: Jan. 13, 1998

[54] METHOD FOR THE PREPARATION OF AN N-VINYL COMPOUND

[75] Inventors: Yoshihiro Honma; Shozo Tanaka, both of Osaka-fu; Mitsuyoshi Oshima, Niigata-ken; Soji Tanioka, Tokyo; Fumiaki Kawamoto, Osaka-fu, all of Japan

[73] Assignee: Shin-Etsu Vinyl Acetate Co., Ltd., Sakai, Japan

[21] Appl. No.: 518,365

[22] Filed: Aug. 23, 1995

[30] Foreign Application Priority Data

Aug. 31, 1994 [JP] Japan ................... 6-206489

[51] Int. Cl.$^6$ ................... C07D 263/20
[52] U.S. Cl. ................... 540/485; 544/97; 546/243; 548/229; 548/231; 548/543; 560/261; 564/187; 564/224
[58] Field of Search ................... 560/261; 548/215, 548/543, 231, 229; 564/205, 187, 224; 540/485; 546/243; 544/97

[56] References Cited

U.S. PATENT DOCUMENTS

| | | | |
|---|---|---|---|
| 3,354,208 | 11/1967 | Welcher | 564/205 |
| 3,526,620 | 9/1970 | Bestian et al. | 540/485 |
| 4,511,722 | 4/1985 | Krimm et al. | 548/231 |
| 4,670,591 | 6/1987 | Oftring et al. | 564/224 |
| 5,039,817 | 8/1991 | Kroker et al. | 548/543 |
| 5,059,713 | 10/1991 | Armor et al. | 564/187 |
| 5,574,185 | 11/1996 | Sato | 564/224 |

FOREIGN PATENT DOCUMENTS

| | | | |
|---|---|---|---|
| 0350666A2 | 1/1990 | European Pat. Off. | |
| 0608690A1 | 8/1994 | European Pat. Off. | |
| 1421336 | 11/1965 | France | |
| 43-8302 | 3/1972 | Japan | |
| 43-8303 | 3/1972 | Japan | |
| 48-44251 | 6/1973 | Japan | |
| 125507 | 1/1960 | U.S.S.R. | |
| 728955 | 4/1955 | United Kingdom | 564/205 |

OTHER PUBLICATIONS

*Chemical Abstracts*, 77(8), abstract No. 49091j (abstract of JP 7–208302) (Aug. 1972).

*Chemical Abstracts*, 77(8), abstract No. 49092k (abstract of JP 7–208303) (Aug. 1972).

*Chemical Abstracts*, 121(13), abstract No. 157520j (abstract of JP 6–145140) (Sep. 1994).

*Primary Examiner*—Donald G. Daus
*Attorney, Agent, or Firm*—Wenderoth, Lind & Ponack

[57] ABSTRACT

Proposed is a novel and very efficient method for the preparation of an N-vinyl compound such as N-vinyl-2-pyrrolidone and N-vinyl-N-ethyl acetamide by the thermal decomposition of an N-(α-acyloxyethyl) compound which is a novel compound obtained by the addition reaction between an NH group-containing compound such as 2-pyrrolidone and N-ethyl acetamide and a vinyl carboxylate, e.g., vinyl acetate, in the presence of an alkali, e.g. alkali metal hydroxide. The reaction mixture after completion of this addition reaction as such, i.e. without isolating the N-(α-acyloxyethyl) compound, such as N-(α-acetoxyethyl)-2-pyrrolidone and N-(α-acetoxyethyl)-N-ethyl acetamide, is heated to effect in situ formation of the desired N-vinyl compound which can then be isolated by distillation under reduced pressure in a very high overall yield.

6 Claims, No Drawings

METHOD FOR THE PREPARATION OF AN N-VINYL COMPOUND

BACKGROUND OF THE INVENTION

The present invention relates to a novel method for the preparation of an N-vinyl compound having usefulness as a reactive monomeric compound for the preparation of special polymeric compounds.

As is known, N-vinyl compounds in general or, in particular, an organic compound in which a carbonyl group and a vinyl group are bonded to the same nitrogen atom, such as N-vinyl-2-pyrrolidone, have good polymerizability and high reactivity so that they are widely used as a class of industrially very important reactive monomers in the preparation of various kinds of specialty polymers and as an ingredient in ultraviolet-curable resin compositions. For example, N-vinyl-2-pyrrolidone is used as a starting monomer in the preparation of polyvinyl pyrrolidone as a typical water-soluble polymer or as an ingredient in an ultraviolet-curable resin composition.

Various methods have been proposed heretofore for the preparation of these N-vinyl compounds. Taking N-vinyl-2-pyrrolidone as a typical example, known methods for the preparation of this compound include: (1) a method in which acetylene and 2-pyrrolidone are reacted under high pressure or in the presence of an acid or alkali as a catalyst as disclosed in U.S. Pat. No. 2,806,847 and French Patent 1,340,350; (2) a method in which a vinyl ether or a vinyl carboxylate and 2-pyrrolidone are reacted in the presence of a mercury salt or a palladium compound as a catalyst as disclosed in Japanese Patent Publications 38-4882, 47-8302, 47-8303, 47-2083 and 47-2001; (3) a method in which N-(α-hydroxyethyl) pyrrolidone or an N-(α-alkoxyethyl) pyrrolidone is subjected to thermal decomposition reaction as disclosed in French Patents 1,534,369 and 1,421,336; (4) a method in which N-(β-hydroxyethyl) pyrrolidone or N-(β-acetoxyethyl) pyrrolidone is subjected to thermal decomposition as disclosed in Japanese Patent Publication 48-44251 and USSR Patent 125,507; and so on.

Among the above described prior art methods, the first method has already been rendered to practice as an industrial process although this method is not very advantageous because the investment for the production plant is high as a consequence of the high-pressure reaction along with a risk due to eventual explosion. The other prior art methods are also industrially not practicable because the yield of the desired products cannot be high enough unless the reaction is conducted under very severe reaction conditions if not to mention the expensiveness of some of the starting materials and the catalyst compounds.

Recently, European Patent EP 0 350 666 disclosed a method for the preparation of an N-vinyl amide such as N-vinyl formamide by the thermal cracking of a carboxylic acid amide at a temperature of 150° to 350° C. in the presence of a porous solid catalyst. Even by setting aside the problem that the cracking temperature is so high as not to ensure practicability of the method, this method has low versatility and is not applicable to the preparation of an N-vinyl compound, in which the nitrogen atom has no hydrogen atom directly bonded thereto such as N-vinyl-2-pyrrolidone and the like.

In view of the above described problems and disadvantages in the prior art methods for the preparation of N-vinyl compounds in general, the inventors have conducted extensive investigations to develop a simple and efficient method for the synthetic preparation of the compound by conducting experiments through a widely different routes starting from a variety of known compounds as well as some novel compounds which are not known in the prior art but supposedly could be a promising precursor material for the synthesis of an N-vinyl compound, in particular, having no nitrogen-bonded hydrogen atom.

SUMMARY OF THE INVENTION

The present invention accordingly has an object to provide a novel and efficient method for the preparation of an N-vinyl compound or, in particular, an organic compound in which a carbonyl group and a vinyl group are bonded to the same nitrogen atom.

Thus, the present invention provides a method for the preparation of an N-vinyl compound represented by either one of the general formulas

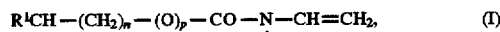

and

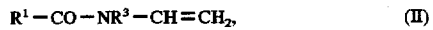

in which $R^1$ is a hydrogen atom or a monovalent hydrocarbon group, $R^3$ is a monovalent hydrocarbon group, the subscript p is 0 or 1 and the subscript n is a positive integer not exceeding 10, which comprises the step of:

heating an N-(α-acyloxyethyl) compound represented by the general formula

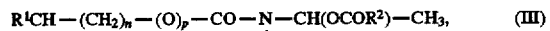

or

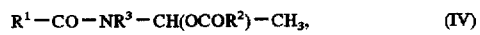

respectively, in which $R^2$ is a hydrogen atom or a monovalent hydrocarbon group and each of the other symbols has the same meaning as defined above, to effect thermal decomposition of the N-(α-acyloxyethyl) compound.

The above mentioned N-(α-acyloxyethyl) compound represented by the general formula (III) or (IV) is a novel compound not known in the prior art but can readily be prepared by the addition reaction between an NH group-containing compound represented by the general formula

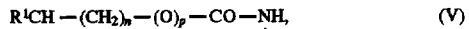

or

respectively, in which each symbol has the same meaning as defined above, and a vinyl carboxylate represented by the general formula

in which $R^2$ has the same meaning as defined above, in the presence of an alkaline substance, e.g., alkali metal hydroxides, as a catalyst.

It is sometimes a very efficient and advantageous method that the reaction mixture after completion of the addition reaction between the NH group-containing compound of the general formula (V) or (VI) and the vinyl carboxylate of the general formula (VII) is directly heated, without isolation of the N-(α-acyloxyethyl) compound therefrom, to effect the thermal decomposition of the N-(α-acyloxyethyl) compound in situ under continuous distillation of the N-vinyl compound as the final product as formed out of the reaction mixture.

DETAILED DESCRIPTION OF THE PREFERRED EMBODIMENTS

As is described above, the inventive method for the preparation of an N-vinyl compound comprises a single step for the thermal decomposition of the N-(α-acyloxyethyl) compound of the above given general formula (III) or (IV), of which it is believed that no synthetic method is known heretofore excepting the above mentioned addition reaction between an NH group-containing compound of the general formula (V) or (VI) and the vinyl carboxylate of the general formula (VII) developed by the inventors. Accordingly, following description is started by the synthetic procedure for the preparation of the N-(α-acyloxyethyl) compound.

The NH group-containing compound as one of the reactants in the addition reaction with the vinyl carboxylate is not particularly limitative provided that a hydrogen atom and a carbonyl group are bonded to the same nitrogen atom in the molecule and can be selected depending on the desired N-vinyl compound. Examples of the NH group-containing compound suitable as the starting material of the N-(α-acyloxyethyl) compound include lactam compounds such as β-propionlactam, 2-pyrrolidone, δ-valerolactam, γ-valerolactam, 2-piperidone, ε-caprolactam, 2-azacyclononanone, 2-azacyclodecanone and the like, oxazolidinone compounds such as 2-oxazolidone, 5-methyl-2-oxazolidone and the like and acid amide compounds such as N-methyl acetamide, N-ethyl acetamide, acetanilide and the like as well as N-substituted derivatives thereof.

The vinyl carboxylate as the other reactant to be reacted with the above described NH group-containing compound is also not limitative including vinyl acetate, vinyl propionate, vinyl butyrate, vinyl pivalate, vinyl benzoate and the like, of which vinyl acetate is preferred in view of the inexpensiveness and availability as an industrial material.

The alkaline substance as a catalyst to promote the addition reaction between the NH group-containing compound and the vinyl carboxylate is selected from the elementary forms of alkali metal and alkaline earth metal elements such as lithium, sodium, potassium, rubidium, cesium, magnesium, calcium and barium as well as compounds thereof such as hydroxides, carbonates, hydrogencarbonates, hydrogenphosphates, acetates and alcoholates, of which alkali metal hydroxides are preferred.

In carrying out the addition reaction between the NH group-containing compound and the vinyl carboxylate, the amount of the vinyl carboxylate can theoretically be equimolar to the NH group-containing compound but it is optional or sometimes advantageous to use an increased amount of up to 2 moles of the vinyl carboxylate per mole of the NH group-containing compound when partial decomposition of the vinyl carboxylate is expected during the reaction or when the reaction product has a relatively high viscosity or relatively high melting point. The reaction mixture consisting of the NH group-containing compound and the vinyl carboxylate can be diluted, if necessary, by the addition of an inert organic solvent such as hexane, benzene, tetrahydrofuran, dioxane and the like. The amount of the alkaline substance as the catalyst is in the range from 0.0001 to 0.2 mole per mole of the NH group-containing compound. The reaction temperature of the addition reaction is in the range from −60° C. to 60° C. or, preferably, from −30° C. to 30° C. Although the addition reaction can proceed at room temperature, it is preferable to conduct the reaction at a relatively low temperature in order to prevent occurrence of side reactions.

Once an N-(α-acyloxyethyl) compound of the general formula (III) or (IV) is obtained in the above described manner, the compound isolated from the reaction mixture is subjected to a thermal decomposition reaction by heating at a temperature in the range from 80° C. to 140° C. or, preferably, from 80° to 110° C., though not particularly limitative thereto. The decomposition reaction of the N-(α-acyloxyethyl) compound is not limited to the thermal decomposition reaction but can proceed as a photochemical reaction by the irradiation with ultraviolet light or as an electrode reaction. It is industrially preferable to conduct the thermal decomposition of the N-(α-acyloxyethyl) compound as contained in the reaction mixture without being isolated therefrom in a condition of distillation under reduced pressure so as to successively take out the N-vinyl compound as produced in the reaction mixture by the thermal decomposition of the N-(α-acyloxyethyl) compound in situ. Since the thermal decomposition of the N-(α-acyloxyethyl) compound can be promoted by an alkaline compound, the reaction mixture after completion of the addition reaction in the presence of an alkaline compound can be subjected as such to the thermal decomposition of the N-(α-acyloxyethyl) compound without removal of the alkaline compound.

Following is a description of a typical but non-limiting procedure for practicing the method of the present invention.

In the first place, an alkaline compound such as an alkali metal hydroxide, e.g., potassium hydroxide, is added to the NH group-containing compound and dissolved therein, if necessary, by gentle warming to form a reaction mixture. Water is formed as a by-product by the side reaction between the NH group and the alkali metal hydroxide so that the reaction mixture is subjected to distillation under reduced pressure to remove the by-product water. Thereafter, the reaction mixture after removal of water is mixed with the vinyl carboxylate so that the addition reaction between the reactants proceeds spontaneously when the reaction mixture is kept at an appropriate temperature to form an N-(α-acyloxyethyl) compound of the general formula (III) or (IV).

The next step is to remove the unreacted vinyl carboxylate and other low boiling point matters from the reaction mixture by a suitable method such as distillation under reduced pressure at a temperature sufficiently low not to cause thermal decomposition of the N-(α-acyloxyethyl) compound. Finally, the temperature of the reaction mixture is increased to, for example, 80° C. to 140° C. so that the thermal decomposition reaction of the N-(α-acyloxyethyl) compound proceeds in the reaction mixture to produce the desired N-vinyl compound along with some by-products such as carboxylic acid, N-acyl compounds, condensation products of acetaldehyde and the like. These decomposition products as produced are successively taken out of the reaction mixture by distillation under reduced pressure and the N-vinyl compound contained in the distillate is isolated therefrom by a suitable known purification procedure such as distillation, recrystallization and the like. It is sometimes the case that an azeotropic mixture is formed between the N-vinyl compound as the product and the carboxylic acid as a by-product to cause a difficulty in the isolation of the product by distillation. This problem can be solved by converting the carboxylic acid into the form of a salt by the neutralization of the distillate with an alkali so as to remove the carboxylic acid in the form of a salt.

In the following, the method of the present invention is described in more detail by way of examples.

EXAMPLE 1

Into a four-necked flask equipped with a stirrer, thermometer and dropping funnel were introduced 172 g (2 moles) of vinyl acetate, into which a solution, which was prepared in advance by dissolving 0.4 g (0.007 mole) of potassium hydroxide in 170 g (2 moles) of 2-pyrrolidone under warming followed by the removal of the by-product water by distillation under reduced pressure and cooling to room temperature, was added dropwise under agitation over a period of 30 minutes while the temperature of the reaction mixture was kept in the range from −20° C. to 10° C. by external cooling to remove the heat of reaction. In the course of the dropwise addition of the solution, a small portion of the reaction mixture was taken and, after removal of the low boiling point materials such as vinyl acetate by distillation under reduced pressure at 60° C., analyzed by the $^1$H- and $^{13}$C-nuclear magnetic resonance absorption spectrometric (NMR) analysis, gas chromatographic-mass spectrometric (GC-MS) analysis and infrared absorption spectrophotometric (IR) analysis under the following conditions to confirm formation of N-(α-acetoxyethyl)-2-pyrrolidone.

NMR Analysis

Apparatus: Model GSK 270 FT-NMR, Nippon Denshi Co.

Solvent: heavy benzene ($d_6$)

Reference for shift in $^1$H-NMR: 0.0 ppm, TMS, external standard

Reference for $^{13}$C-NMR: 128.0 ppm (solvent)

Temperature: room temperature

GC-MS Analysis

Apparatus: Model Hitachi M-80B, GC-MS

Method: direct introduction method, chemical ionization method with isobutane

IR Analysis

Apparatus: Fourier-transformation infrared spectrophotometer Model JIR-5500, Nippon Denshi Co.

Method: KBr tablet method

After completion of the dropwise addition of the 2-pyrrolidone solution, the flask was equipped with a distillation column suitable for distillation under reduced pressure and a condenser and the temperature of the reaction mixture in the flask was increased up to 80° C. along with reduction of the pressure down to 50 mmHg. Thereafter, the temperature of the reaction mixture was gradually increased along with gradual decrease of the pressure finally to reach 1 mmHg when the temperature was 100° C. so that the thermal decomposition reaction of the N-(α-acetoxyethyl)-2-pyrrolidone proceeded in the reaction mixture with simultaneous removal of the thermal decomposition products from the reaction mixture by distillation. The distillate as collected was subjected to a purification treatment of the principal product to obtain N-vinyl-2-pyrrolidone in a yield of 91% of the theoretical value based on the amount of the 2-pyrrolidone used as the starting material.

The identification of the final product was performed by the NMR and IR analyses to give results which were in good coincidence with the data appearing in literatures for this known compound. The molecular weight determined by the GC-MS analysis was 111, which was the value calculated for N-vinyl-2-pyrrolidone having a molecular formula of $C_6H_9ON$.

EXAMPLES 2 to 8

The experimental procedure in each of these examples was substantially the same as in Example 1 excepting replacement of 0.007 mole (0.4 g) of the potassium hydroxide with another alkaline substance including sodium metal, alkali and alkaline earth hydroxides and alkali ethoxylate in an amount given there. The final product in each example was N-vinyl-2-pyrrolidone as identified from the analytical results and the yield of this final product in each example is shown in Table 1. The intermediate compound was identified also to be N-(α-acetoxyethyl)-2-pyrrolidone.

TABLE 1

| Example No. | Alkaline substance | Amount of alkaline substance, moles | Yield, % |
|---|---|---|---|
| 2 | sodium metal | 0.006 | 84.4 |
| 3 | lithium hydroxide | 0.008 | 67.2 |
| 4 | sodium hydroxide | 0.008 | 84.3 |
| 5 | rubidium hydroxide | 0.007 | 93.0 |
| 6 | cesium hydroxide | 0.006 | 94.3 |
| 7 | barium hydroxide | 0.009 | 86.4 |
| 8 | sodium ethoxylate | 0.004 | 84.0 |

EXAMPLE 9

The experimental procedure was substantially the same as in Example 1 excepting replacement of 2 moles of vinyl acetate with the same molar amount (228 g) of vinyl n-butyrate. The intermediate compound could be identified to be N-(α-butyryloxyethyl)-2-pyrrolidone from the results of the instrumental analyses. The final product was also N-vinyl-2-pyrrolidone and the yield thereof was 90.0% of the theoretical value.

EXAMPLE 10

The experimental procedure was substantially the same as in Example 1 excepting increase of the amount of potassium hydroxide to 0.8 g (0.014 mole) and replacement of 2 moles of vinyl acetate with the same molar amount (256 g) of vinyl pivalate. The intermediate compound could be identified to be N-(α-pivaloyloxyethyl)-2-pyrrolidone from the results of the instrumental analyses. The final product was also N-vinyl-2-pyrrolidone and the yield thereof was 95.5% of the theoretical value.

EXAMPLE 11

The experimental procedure was substantially the same as in Example 1 excepting increase of the amount of potassium hydroxide to 1 g (0.018 mole) and replacement of 2 moles of vinyl acetate with the same molar amount (296 g) of vinyl benzoate. The intermediate compound could be identified to be N-(α-benzoyloxyethyl)-2-pyrrolidone from the results of the instrumental analyses. The final product was also N-vinyl-2-pyrrolidone and the yield thereof was 85% of the theoretical value.

EXAMPLE 12

A solution was prepared by dissolving 9 g (0.06 mole) of cesium hydroxide in 198 g (2 moles) of δ-valerolactam under gentle warming followed by removal of the by-product water by distillation under reduced pressure and addition of 240 ml of tetrahydrofuran to be cooled to room temperature.

The subsequent experimental procedure was substantially the same as in Example 1 excepting increase of the amount of vinyl acetate to 206 g (2.4 moles) and replacement of the potassium hydroxide solution in 2-pyrrolidone with the above prepared cesium hydroxide solution in δ-valerolactam. The intermediate compound could be identified to be N-(α-acetoxyethyl)-δ-valerolactam from the results of the instrumental analyses. The final product was identified to be N-vinyl-δ-valerolactam having a molecular weight of 125 from the results of the instrumental analyses to give results which were in good coincidence with the literature data for this known compound and the yield thereof was 84% of the theoretical value.

EXAMPLE 13

A solution was prepared by dissolving 4.5 g (0.03 mole) of cesium hydroxide in 226 g (2 moles) of ε-caprolactam under gentle warming followed by removal of the by-product water by distillation under reduced pressure and addition of 300 ml of benzene to be cooled to room temperature.

The subsequent experimental procedure was substantially the same as in Example 1 excepting increase of the amount of vinyl acetate to 240 g (2.8 moles) and replacement of the potassium hydroxide solution in 2-pyrrolidone with the above prepared cesium hydroxide solution in ε-caprolactam. The intermediate compound could be identified to be N-(α-acetoxyethyl)-ε-caprolactam from the results of the instrumental analyses. The final product was identified to be N-vinyl-ε-caprolactam having a molecular weight of 139 from the results of the instrumental analyses to give results which were in good coincidence with the literature data for this known compound and the yield thereof was 88% of the theoretical value.

EXAMPLE 14

A solution was prepared by dissolving 6 g (0.04 mole) of cesium hydroxide in 174 g (2 moles) of 2-oxazolidone under gentle warming followed by removal of the by-product water by distillation under reduced pressure and addition of 600 ml of tetrahydrofuran to be cooled to room temperature.

The subsequent experimental procedure was substantially the same as in Example 1 excepting replacement of the potassium hydroxide solution in 2-pyrrolidone with the above prepared cesium hydroxide solution in 2-oxazolidone. The intermediate compound could be identified to be N-(α-acetoxyethyl)-2-oxazolidinone from the results of the instrumental analyses. The final product was identified to be N-vinyl-2-oxazolidinone having a molecular weight of 113 from the results of the instrumental analyses to give results which were in good coincidence with the literature data for this known compound and the yield thereof was 77% of the theoretical value.

EXAMPLE 15

A solution was prepared by dissolving 2.0 g (0.036 mole) of potassium hydroxide in 146 g (2 moles) of N-methyl acetamide under gentle warming followed by removal of the by-product water by distillation under reduced pressure and addition of 20 ml of benzene to be cooled to room temperature.

The subsequent experimental procedure was substantially the same as in Example 1 excepting increase of the amount of vinyl acetate to 190 g (2.2 moles) and replacement of the potassium hydroxide solution in 2-pyrrolidone with the above prepared potassium hydroxide solution in N-methyl acetamide. The intermediate compound could be identified to be N-(α-acetoxyethyl)-N-methyl acetamide from the results of the instrumental analyses. The final product was identified to be N-vinyl-N-methyl acetamide having a molecular weight of 99 from the results of the instrumental analyses to give results which were in good coincidence with the literature data for this known compound and the yield thereof was 80% of the theoretical value.

EXAMPLE 16

A solution was prepared by dissolving 12 g (0.08 mole) of cesium hydroxide in 174 g (2 moles) of N-ethyl acetamide under gentle warming followed by removal of the by-product water by distillation under reduced pressure and addition of 80 ml of tetrahydrofuran to be cooled to room temperature.

The subsequent experimental procedure was substantially the same as in Example 1 excepting replacement of the potassium hydroxide solution in 2-pyrrolidone with the above prepared cesium hydroxide solution in N-ethyl acetamide. The intermediate compound could be identified to be N-(α-acetoxyethyl)-N-ethyl acetamide from the results of the instrumental analyses. The final product was identified to be N-vinyl-N-ethyl acetamide having a molecular weight of 113 from the results of the instrumental analyses to give results which were in good coincidence with the literature data for this known compound and the yield thereof was 84% of the theoretical value.

What is claimed is:

1. A method for the preparation of an N-vinyl compound represented by either one of the formulas

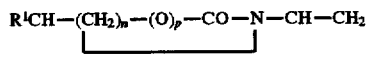

and

in which $R^1$ is a hydrogen atom or a monovalent hydrocarbon group, $R^3$ is a monovalent hydrocarbon group, the subscript p is 0 or 1 and the subscript n is a positive integer not exceeding 10, which comprises the steps of:

(a) mixing an NH group-containing compound represented by the formula

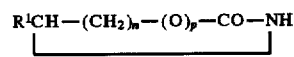

or

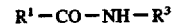

respectively, in which each symbol has the same meaning as defined above, and a vinyl carboxylate represented by the formula

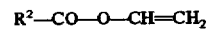

in which $R^2$ is a hydrogen atom or a monovalent hydrocarbon group, in the presence of an alkaline substance which is an alkali or alkaline earth metal compound to form an N-(α-acyloxyethyl) compound represented by the formula

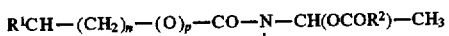

or

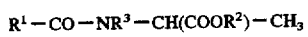

respectively, in which each symbol has the same meaning as defined above, as an addition product between the NH group-containing compound and the vinyl carboxylate in the mixture; and (b) heating the mixture containing the N-(α-acyloxyethyl) compound to effect thermal decomposition of the N-(α-acyloxyethyl) compound.

2. The method for the preparation of an N-vinyl compound as claimed in claim 1 in which heating of the mixture in step (b) is performed under concurrent distillation of the N-vinyl compound as produced from the N-(α-acyloxyethyl) compound in the mixture.

3. The method for the preparation of an N-vinyl compound as claimed in claim 1 in which the temperature in step (b) is in the range from 80° to 140° C.

4. The method according to claim 1, wherein the alkaline substance is an alkali metal or alkaline earth metal hydroxide, carbonate, hydrogen carbonate, hydrogen phosphate, acetate or alcoholate.

5. The method according to claim 1, wherein the alkaline substance is an alkali metal hydroxide.

6. The method according to claim 1, where unreacted vinyl carboxylate from step (a) is removed prior to heating in step (b).

* * * * *